US00PP26939P2

(12) United States Plant Patent
Dummen

(10) Patent No.: US PP26,939 P2
(45) Date of Patent: Jul. 12, 2016

(54) ***PELARGONIUM* PLANT NAMED 'DUEVIBU14'**

(50) Latin Name: *Pelargonium zonale*
Varietal Denomination: Duevibu14

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 138 days.

(21) Appl. No.: 14/120,812

(22) Filed: Jul. 1, 2014

(51) Int. Cl.
*A01H 5/02* (2006.01)

(52) U.S. Cl.
USPC ..... Plt./329

(58) Field of Classification Search
USPC ..... Plt./329
See application file for complete search history.

*Primary Examiner* — Keith Robinson
(74) *Attorney, Agent, or Firm* — C. A. Whealy

(57) ABSTRACT

A new and distinct cultivar of Zonal Geranium plant named 'Duevibu14', characterized by its upright plant habit; vigorous growth habit; freely basal branching habit; dark green-colored leaves; freely flowering habit; large red purple-colored flowers; and good garden performance.

1 Drawing Sheet

Botanical designation: *Pelargonium zonale.*
Cultivar denomination: 'DUEVIBU14'.

BACKGROUND OF THE INVENTION

The present invention relates to a new and distinct cultivar of Zonal Geranium plant, botanically known as *Pelargonium zonale,* and hereinafter referred to by the name 'Duevibu14'.

The new Zonal Geranium plant is a product of a planned breeding program conducted by the Inventor in Rheinberg, Germany. The objective of the breeding program is to create new vigorous Zonal Geranium plants with dark-colored leaves and numerous attractive flowers.

The new Zonal Geranium plant originated from a cross-pollination made by the Inventor in July, 2008 in Rheinberg, Germany of a proprietary selection of *Pelargonium zonale* identified as code number AK8702, not patented, as the female, or seed, parent with a proprietary selection of *Pelargonium zonale* identified as code number Z02-0041-001, not patented, as the male, or pollen, parent. The new Zonal Geranium plant was discovered and selected by the Inventor as a single flowering plant from within the progeny of the stated cross-pollination in a controlled greenhouse environment in Rheinberg, Germany in May, 2013.

Asexual reproduction of the new Zonal Geranium plant by vegetative terminal cuttings in a controlled greenhouse environment in Rheinberg, Germany since June, 2013 has shown that the unique features of this new Zonal Geranium plant are stable and reproduced true to type in successive generations.

SUMMARY OF THE INVENTION

Plants of the new Zonal Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duevibu14'.

These characteristics in combination distinguish 'Duevibu14' as a new and distinct Zonal Geranium plant:

1. Upright plant habit.
2. Vigorous growth habit.
3. Freely basal branching habit.
4. Dark green-colored leaves.
5. Freely flowering habit.
6. Large red purple-colored flowers.
7. Good garden performance.

Plants of the new Zonal Geranium differ primarily from plants of the female parent selection in plant habit as plants of the new Zonal Geranium are more compact than plants of the female parent selection.

Plants of the new Zonal Geranium differ primarily from plants of the male parent selection in growth habit as plants of the new Zonal Geranium are more vigorous than plants of the male parent selection. In addition, plants of the new Zonal Geranium and the male parent selection differ in flower color as plants of the male parent selection have pink-colored flowers.

Plants of the new Zonal Geranium can be compared to plants of the *Pelargonium zonale* 'Fiona', not patented. In side-by-side comparisons conducted in Rheinberg, Germany, plants of the new Zonal Geranium differed primarily from plants of 'Fiona' in the following characteristics:

1. Plants of the new Zonal Geranium were more compact than plants of 'Fiona'.
2. Plants of the new Zonal Geranium had smaller leaves than plants of 'Fiona'.
3. Plants of the new Zonal Geranium had smaller flowers and inflorescences than plants of 'Fiona'.
4. Plants of the new Zonal Geranium and 'Fiona' differed slightly in flower color.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Duevibu14' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices typical of commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 2007 Edition, except where general terms of ordinary dictionary significance are used.

Botanical classification: *Pelargonium zonale* 'Duevibu14'.

Parentage:

*Female, or seed, parent*.—Proprietary selection of *Pelargonium zonale* identified as code number AK8702, not patented.

*Male or pollen parent*.—Proprietary selection of *Pelargonium zonale* identified as code number Z02-0041-001, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous.

*Rooting habit*.—Freely branching; dense.

Plant description:

*Plant and growth habit*.—Upright plant habit; uniformly rounded; densely foliated; vigorous growth habit.

*Branching habit*.—Freely basal branching habit with about seven basal branches developing per plant.

*Plant height to top of flower umbels*.—About 28 cm.

*Plant height to top of foliar plane*.—About 20 cm.

*Plant width*.—About 51 cm.

*Lateral branches*.—Length: About 13 cm. Diameter: About 8 mm. Internode length: About 1.75 cm. Texture: Pubescent. Strength: Moderately strong. Color: Close to 146B.

Leaf description:

*Arrangement*.—Alternate; simple.

*Length*.—About 4.4 cm.

*Width*.—About 7.1 cm.

*Shape*.—Roughly reniform.

*Apex*.—Acute.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to N137D. Developing leaves, lower surface: Close to 147B. Fully expanded leaves, upper surface: Close to N137A; venation, close to 147B. Fully expanded leaves, lower surface: Close to 147B; venation, close to 147B.

*Zonation pattern*.—Distance from margin: About 2.4 cm. Width: About 2.8 cm. Color: Close to 147A.

*Petioles*.—Length: About 6.1 cm. Diameter: About 2 mm. Texture, upper and lower surfaces: Smooth, glabrous. Color, upper and lower surfaces: Close to 144A.

Flower description:

*Flower arrangement*.—Single type flowers arranged in rounded hemispherical umbels arising from apical leaf axils; umbels displayed above the foliar plane on moderately strong peduncles; flowers face mostly upright to outwardly.

*Fragrance*.—None detected.

*Flowering habit*.—Freely flowering habit, about seven to 35 flowers per umbel and about 15 flower umbels developing per plant.

*Flowering season*.—Year-round under greenhouse conditions; in outdoor nurseries and gardens in Germany, flowering is continuous from spring throughout the summer until the autumn; plants begin to flower about eight weeks after planting.

*Flower longevity*.—Individual flowers last about five to seven days on the plant; flowers persistent.

*Umbel height*.—About 5.5 cm.

*Umbel diameter*.—About 9.5 cm.

*Flower diameter*.—About 3.6 cm by 4.7 cm.

*Flower depth* (*height*).—About 2.2 cm.

*Flower buds*.—Length: About 1.4 cm. Diameter: About 8.4 mm. Shape: Ovoid. Color: Close to N57A.

*Petals*.—Quantity per flower: About five arranged in a single whorl. Length: About 2.3 cm. Width: About 2 cm. Shape: Obovate. Apex: Rounded. Base: Attenuate. Margin: Sinuate. Texture, upper and lower surfaces: Smooth, glabrous. Color: When opening and fully opened, upper surface: Close to N57A and 68B; colors becoming closer to 61B with development. When opening and fully opened, lower surface: Close to N66B; color becoming closer to 61B with development.

*Petaloids*.—None observed.

*Sepals*.—Quantity per flower: Five arranged in a single whorl. Length: About 1 cm. Width: About 2.8 mm. Shape: Ensiform. Apex: Apiculate. Margin: Entire. Texture, upper and lower surfaces: Smooth, glabrous. Color, upper and lower surfaces: Close to 146C.

*Peduncles* (*umbel stems*).—Length: About 9.5 cm. Diameter: About 3.8 mm. Strength: Moderately strong. Texture: Smooth, glabrous. Color: Close to 144A.

*Pedicels* (*individual flower stems*).—Length: About 2.2 cm. Diameter: About 1.5 mm. Strength: Moderately strong. Texture: Smooth, glabrous. Color: Close to 146A.

*Reproductive organs*.—Androecium: Stamen quantity per flower: About eleven. Filament length: About 2.4 mm. Filament color: Close to 64B. Anther length: About 2.2 mm. Anther shape: Oblong. Anther color: Close to 46B. Pollen amount: Moderate. Pollen color: Close to 28A. Gynoecium: Pistil quantity per flower:

One. Pistil length: About 3 mm. Stigma shape: Tapering. Stigma color: Close to 60A. Style length: About 2 mm. Style color: Close to 65B. Ovary color: Close to 144C.

*Seeds and fruits*.—Seed and fruit development have not been observed on plants of the new Zonal Geranium.

Disease & pest resistance: Plants of the new Zonal Geranium have not been observed to be resistant to pathogens and pests common to Zonal Geranium plants.

Garden performance: Plants of the new Zonal Geranium have been observed have good garden performance and to tolerate rain, wind, and temperatures ranging from about 5° C. to about 40° C.

It is claimed:

1. A new and distinct Zonal Geranium plant named 'Duevibu14' as illustrated and described.

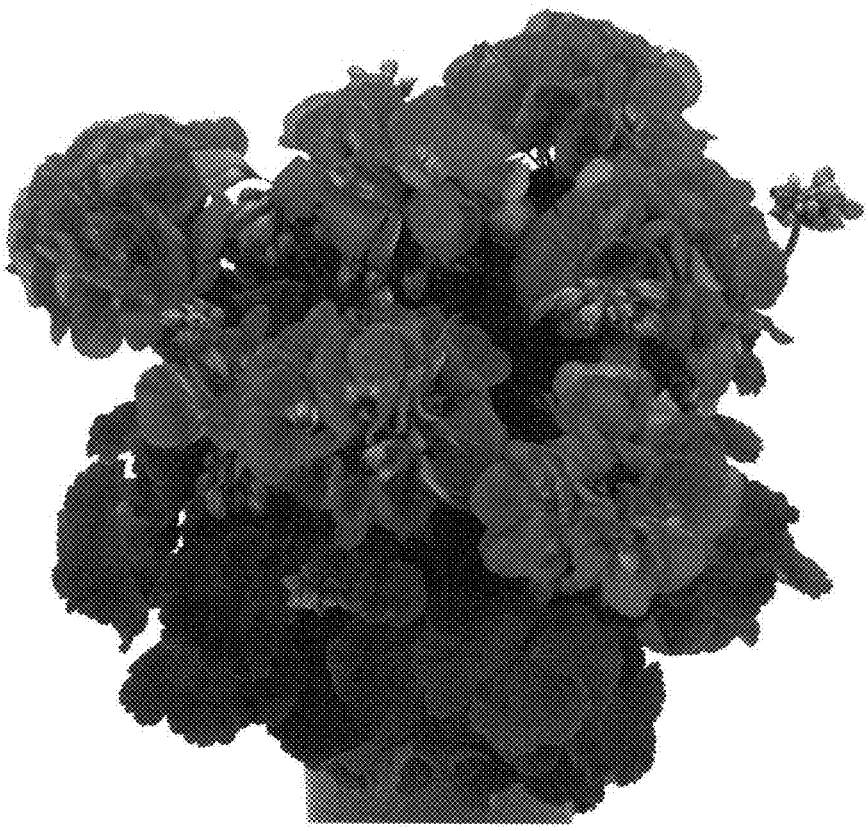

* * * * *